(12) United States Patent
Kamei et al.

(10) Patent No.: US 9,758,463 B1
(45) Date of Patent: Sep. 12, 2017

(54) METHOD FOR PRODUCING VAPOR COMPOSITION CONTAINING LACTIC ACID

(71) Applicant: NIPPON SHOKUBAI CO., LTD., Osaka-shi, Osaka (JP)

(72) Inventors: Hisashi Kamei, Osaka (JP); Hiroshi Yoshida, Osaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 15/511,158

(22) PCT Filed: Sep. 17, 2015

(86) PCT No.: PCT/JP2015/076462
§ 371 (c)(1),
(2) Date: Mar. 14, 2017

(87) PCT Pub. No.: WO2016/043264
PCT Pub. Date: Mar. 24, 2016

(30) Foreign Application Priority Data

Sep. 17, 2014 (JP) .................... 2014-188694

(51) Int. Cl.
*C07C 59/08* (2006.01)
*B01B 1/00* (2006.01)

(52) U.S. Cl.
CPC ............ *C07C 59/08* (2013.01); *B01B 1/005* (2013.01)

(58) Field of Classification Search
CPC .................................................. C07C 59/08
(Continued)

(56) References Cited

U.S. PATENT DOCUMENTS

| 2,859,240 A | 11/1958 | Holmen |
| 4,786,756 A | 11/1988 | Paparizos et al. |

(Continued)

FOREIGN PATENT DOCUMENTS

| CH | WO 2005095320 A1 * | 10/2005 | ........... C07C 51/377 |
| JP | 56-065841 | 6/1981 | |

(Continued)

OTHER PUBLICATIONS

Zhang, et al., "Catalytic Dehydration of Lactic Acid to Acrylic Acid Over Sulfate Catalysts", The Canadian Journal of Chemical Engineering, vol. 86, Dec. 2008, pp. 1047-1053.

*Primary Examiner* — Deborah D Carr
(74) *Attorney, Agent, or Firm* — Hamre, Schumann, Mueller & Larson, P.C.

(57) ABSTRACT

The method for producing a vapor composition containing lactic acid of the present invention is capable of suppressing the generation of by-products such as acetaldehyde and carbon monoxide due to pyrolysis of a lactic acid species during vaporization. Furthermore, a lactic acid oligomer generated can be effectively used without loss, and a vapor composition containing lactic acid can be industrially efficiently produced stably for a long time. The present invention relates to a method for producing a vapor composition containing lactic acid including: feeding a liquid composition containing lactic acid to a vaporizer; mixing the liquid composition with a liquid composition containing a lactic acid oligomer contained in the vaporizer to prepare a liquid mixture; and heating the liquid mixture to vaporize part of the liquid mixture, whereby a vapor composition containing lactic acid is produced.

9 Claims, 1 Drawing Sheet (58) Field of Classification Search
USPC .......................................................... 562/589
See application file for complete search history.

(56) References Cited

U.S. PATENT DOCUMENTS

| | | |
|---|---|---|
| 5,543,494 A | 8/1996 | Perego et al. |
| 6,489,508 B1 | 12/2002 | Van Gansbeghe et al. |
| 6,630,603 B1 | 10/2003 | Van Breugel et al. |
| 7,875,153 B2 | 1/2011 | Winkelaar et al. |

FOREIGN PATENT DOCUMENTS

| | | | |
|---|---|---|---|
| JP | 5665841 A | * | 6/1981 |
| JP | 2011-074084 | | 4/2011 |
| JP | 201174084 A | * | 4/2011 |
| WO | 2005/095320 | | 10/2005 |
| WO | 2015/016217 | | 2/2015 |

* cited by examiner

METHOD FOR PRODUCING VAPOR COMPOSITION CONTAINING LACTIC ACID

TECHNICAL FIELD

The present invention relates to a method for producing a vapor composition containing lactic acid. Specifically, the present invention relates to a method for producing a vapor composition containing lactic acid effectively used to produce chemicals made from lactic acid.

BACKGROUND ART

Many chemicals have been produced using materials originated from coal, petroleum, or other fossil materials. However, for the prevention of the global warming and the protection of the environment, the use of renewable biological resources as carbon resources has been recently attracted the attention as an alternative to conventional fossil materials. For example, techniques of the use of biomass resources have been developed. Examples of the biomass resources include starch-based biomass such as corn or wheat, sugar-based biomass such as sugarcane, and cellulose-based biomass such as rapeseed cake or rice straw.

For example, polylactic acid derived from lactic acid (lactic acid monomer) that is produced from sugar by fermentation is a typical chemical made from biomass. Further, the use of lactic acid as raw materials for other chemicals has been investigated. For example, lactic acid esters are used as solvents, and have been investigated for conversion to an acrylic acid species or a pyruvic acid species.

The reactions for producing other chemicals from lactic acid include a gas-phase reaction in which chemicals are produced by vaporizing raw materials including lactic acid and bringing the vapor into contact with a catalyst.

For example, gas-phase dehydration using a solid catalyst is known as a technique for the production of acrylic acid from lactic acid (Non-Patent Literature 1 described below).

Further, Patent Literature 1 discloses a method for synthesizing an α,β-unsaturated carboxylic acid by introducing an aqueous solution of an α- or β-hydroxy carboxylic acid to a packed portion of inert ceramic or the like or an acidic solid catalyst, and heating the solution.

CITATION LIST

Patent Literature

Patent Literature 1: WO 2005/095320

Non-Patent Literature

Non-Patent Literature 1: The Canadian Journal of Chemical Engineering. 86, 1047-1053 (2008)

SUMMARY OF INVENTION

Technical Problem

In gas-phase dehydration reactions of lactic acid described in the literature documents, a catalyst is packed in a reactor and an inert filler is placed in front of the catalyst layer as a vaporization layer, and an aqueous solution of lactic acid is fed to the reactor. That is, gas-phase dehydration reactions are intended to evaporate the whole aqueous solution of lactic acid fed and bring the vapor into contact with a catalyst. If an aqueous solution of lactic acid is vaporized in such a way, water initially mainly evaporates from a heated aqueous solution of lactic acid because there is a large difference in the boiling point between lactic acid and water. As a result, the lactic acid is concentrated in the liquid phase, leading to a gradual increase in the evaporation temperature (boiling point). In addition, since lactic acid is a hydroxy carboxylic acid, the molecules of the lactic acid are readily intermolecularly esterified to form a lactic acid oligomer due to the increased concentration of lactic acid and the increased boiling point of the liquid phase, leading to a further increase in the evaporation temperature. At very high evaporation temperature, lactic acid or a lactic acid oligomer is pyrolyzed, leading to the generation of loss of a lactic acid species. In addition to this, the produced pyrolysates may negatively affect processes following the evaporation. Examples of the pyrolysates of a lactic acid species include acetaldehyde, propionic acid, 2,3-pentanedione, carbon monoxide, and carbon dioxide. Finally, as the evaporation of the raw material liquid proceeds and the amount of the liquid is reduced, the liquid has a very high boiling point and is mainly composed of lactic acid and a lactic acid oligomer(s). A lactic acid oligomer, particularly a lactic acid oligomer having a high molecular weight containing three or more lactic acid monomer units, is less likely to evaporate and thus left in a vaporizer (evaporator), leading to the generation of loss of a lactic acid oligomer, clogging of tubes, or staining in tubes due to the oligomer turned into a carbonaceous material. Further, since the evaporation temperature (boiling point) of the raw material liquid increases as the evaporation proceeds, the solution has a very high temperature in the latter half of the evaporation. Therefore, lactic acid or a lactic acid oligomer is pyrolyzed to generate acetaldehyde, carbon monoxide, or propionic acid, leading to a reduction in the amount of the resulting lactic acid vapor. As described above, in cases where an aqueous solution of lactic acid is completely evaporated, the constitution and the boiling point of the liquid phase are significantly changed between the beginning and the end of the evaporation, leading to oligomerization or pyrolysis to generate the loss of a lactic acid species. Thus, the solution is difficult to efficiently evaporate.

Furthermore, the present inventors found that since the rate of the oligomerization reaction of lactic acid is very high, oligomerization is difficult to completely prevent in the industrial scale even if it is suppressed by evaporating the liquid composition containing lactic acid by a technique of low-thermal history.

Solution to Problem

The problems of the present invention can be solved in the following way.

The present invention relates to a method for producing a vapor composition containing lactic acid including:

mixing a liquid composition containing lactic acid fed to a vaporizer with a liquid composition containing a lactic acid oligomer contained in the vaporizer to prepare a liquid mixture; and heating the liquid mixture to vaporize part of the liquid mixture, whereby a vapor composition containing lactic acid is produced.

Preferably, the liquid composition containing lactic acid is added to and mixed with the liquid composition containing a lactic acid oligomer, and simultaneously the resulting liquid mixture is heated so that part of the liquid mixture is vaporized.

A mass ratio of lactic acid dimer to lactic acid (lactic acid dimer/lactic acid) contained in the liquid composition containing a lactic acid oligomer is preferably 0.4 to 3.

An average residence time of the liquid mixture in the vaporizer at a temperature in the range of 210° C. or higher is preferably 300 minutes or less.

That is, a vapor is produced not only from the liquid composition containing lactic acid fed to a vaporizer, but also from part of a liquid mixture of the liquid composition containing lactic acid and the liquid composition containing a lactic acid oligomer contained in the vaporizer. As a result, an increase in the temperature of the liquid in the vaporizer can be suppressed, and the generation of by-products due to pyrolysis can be suppressed. Further, the inventors completed a technique capable of producing a vapor composition containing lactic acid stably for a long time. In this technique, an oligomer generated in the vaporizer can be effectively used, and the attachment of heavy components in the vaporizer can be suppressed, for example.

Advantageous Effects of Invention

The method for producing a vapor composition containing lactic acid of the present invention is capable of suppressing the generation of by-products such as acetaldehyde and carbon monoxide due to pyrolysis of a lactic acid species during vaporization. Furthermore, a lactic acid oligomer generated during vaporization can be effectively used without loss, and the evaporation efficiency of the lactic acid can be enhanced. In addition, a method can be provided in which the attachment of heavy compounds such as an oligomer can be prevented, and the vapor composition containing lactic acid can be industrially efficiently produced stably for a long time.

DESCRIPTION OF EMBODIMENTS

The present invention is described based on the embodiments described below, but is not limited to these embodiments.

A combination of two or more of preferred embodiments of the present invention described below is also a preferred embodiment of the present invention.

The liquid composition containing lactic acid fed to a vaporizer used in the present invention (hereinafter, also referred to as a raw material composition A) may be produced by a fermentation method, which is a common production method, or may be produced by a chemical method. Lactic acid is usually available in the form of an aqueous solution, and the solution may be used as it is, may be used after dilution with a solvent such as water, or may be used after appropriate concentration by removing water by evaporation, for example. The water for dilution may be ion exchange water, pure water, or tap water. Wastewater generated in the production process may be recycled and used. The liquid composition containing lactic acid may contain a lactic acid oligomer or a condensation product of lactic acid such as lactide in addition to lactic acid.

The vaporizer herein includes a heating part, a heating source to heat the heating part, a tube, and liquid delivery equipment. Separately from the heating part, the vaporizer may include a gas-liquid separation tank. Examples of the tube include a tube for feeding a raw material composition, a tube for circulating an oligomer composition, and a tube for extracting a vapor composition containing lactic acid. One or more of these may be used. Examples of the liquid delivery equipment include a pump for feeding a raw material composition and a pump for circulating an oligomer composition. One or more of these may be used.

The raw material composition A used in the present invention may contain components other than lactic acid, a lactic acid oligomer, and lactide (hereinafter, also referred to as a lactic acid species). Examples of the components include solvents. The solvents are preferably those capable of dissolving a lactic acid species. Examples thereof include water, alcohol, hydrocarbon, ether, ketone, ester, amine, and amide. These may be used alone or two or more of these may be used in combination. In particular, water is preferred. In the presence of water, a lactic acid oligomer or lactide is hydrolyzed to increase the concentration of lactic acid, leading to expectations of good evaporation efficiency of a lactic acid species.

The concentration of the lactic acid species in the raw material composition A is preferably 5% by mass or more, more preferably 10% by mass or more, still more preferably 15% by mass or more, still further more preferably 20% by mass or more. At too low a concentration, excessive energy is required for evaporation.

The concentration of the lactic acid species herein refers to the concentration of the lactic acid, the lactic acid oligomer, and the lactide.

The present invention relates to a method for efficiently producing a vapor composition containing lactic acid capable of sufficiently preventing the generation of loss of lactic acid due to oligomerization during evaporation.

The production method of the present invention includes mixing the raw material composition A with a liquid composition containing a lactic acid oligomer contained in a vaporizer (hereinafter, also referred to as oligomer composition B) to prepare a liquid mixture; and heating the liquid mixture to vaporize part of the liquid mixture, whereby a vapor composition containing lactic acid is produced. For example, preferably, the raw material composition A is added to and mixed with the oligomer composition B, and simultaneously the resulting liquid mixture is heated so that part of the liquid mixture is vaporized. In this case, part of the mixture of the raw material composition A and the oligomer composition B is vaporized while the raw material composition A is added to the oligomer composition B. In other words, the preferred embodiments of the present invention include an embodiment in which the vapor composition containing lactic acid is produced by vaporizing part of the liquid mixture in the vaporizer while the raw material composition A is added to the liquid mixture containing a lactic acid oligomer in the vaporizer.

The oligomer composition B may be any composition containing a lactic acid oligomer, and is preferably a mixture containing a lactic acid oligomer, lactic acid, and water. The lactic acid oligomer in the oligomer composition B includes at least lactic acid dimer, and may include a lactic acid oligomer composed of three or more lactic acid monomer units. In the oligomer composition B, the mass ratio of the lactic acid dimer to the lactic acid (lactic acid dimer/lactic acid) is preferably 0.4 or more, more preferably 0.5 or more, still more preferably 0.6 or more, particularly preferably 0.8 or more. The mass ratio is preferably 3 or less, more preferably 2.5 or less, still more preferably 2.0 or less. If the mass ratio is less than 0.4, the concentration of water in the oligomer composition B needs to be increased in order to control the mass ratio to less than 0.4. In this case, since water has a high vapor pressure, the concentration of water in the generated vapor significantly increases, which may lead to a reduction in the concentration of lactic acid. If the mass ratio is more than 3, the boiling point may be very high, and, as a result, the generation efficiency of vapor may be poor or pyrolysis may lead to a reduction in the amount of a lactic acid species obtained as vapor.

There is an oligomer distribution of lactic acid oligomer in the oligomer composition B, and the lactic acid oligomer includes a lactic acid oligomer composed of three or more lactic acid monomer units. If the proportion of a long-chain lactic acid oligomer increases, the boiling point may be high, and, as a result, the generation efficiency of vapor may be poor or pyrolysis may lead to a reduction in the amount of a lactic acid species obtained as vapor. The total amount of lactic acid oligomers from dimer to decamer is preferably 50% by mass or more, more preferably 60% by mass or more of the entire lactic acid oligomer. The total amount of lactic acid oligomers from dimer to pentamer is preferably 30% by mass or more of the entire lactic acid oligomer, more preferably 40% by mass or more, still more preferably 50% by mass or more.

The lactic acid oligomer herein may include lactic acid oligomers from dimer to 100-mer.

The oligomer composition B is contained in a vaporizer, and has only to be contained in any of instruments composing the vaporizer, such as a heating part, a tube, and a gas-liquid separation tank, which are exemplified below, and has only to be mixed with the raw material composition A therein. The temperature of the oligomer composition B contained in the vaporizer depends on the operation conditions of the vaporizer, and is maintained within the range of 25° C. to the boiling point of the oligomer composition B at an operating pressure. The temperature may vary in the respective instruments. For example, there may be a temperature distribution inside the tube.

Compared to the case of vaporizing the raw material composition A alone, mixing the raw material composition A with the oligomer composition B and evaporating part of the resulting liquid mixture, particularly, adding the raw material composition A to the oligomer composition B and mixing them while evaporating part of the resulting liquid mixture less changes the constitution of the liquid phase during evaporation, and further less changes the evaporation temperature. Accordingly, the liquid is prevented from being concentrated to a liquid with a high concentration of an oligomer, and pyrolysis due to an increase in the temperature is suppressed.

The lactic acid in the raw material composition A may be oligomerized after mixed with the oligomer composition B in the vaporizer depending on the constitution. Such oligomerization proceeds only until the composition reaches an equilibrium, and the oligomerization does not proceed endlessly. In the liquid mixture, the oligomerization reaction of lactic acid and the hydrolysis reaction of a lactic acid oligomer are simultaneously occur and are in equilibrium, and the constitution of the liquid mixture is kept constant under the stable conditions. Therefore, the loss of a lactic acid oligomer due to excessive generation thereof is prevented, or even if the oligomerization of lactic acid proceeds, the oligomer can be effectively used.

The present invention is described with reference to FIG. 1, for example. The vaporizer shown in FIG. 1 includes a tank (1) for the raw material composition A, a feed pump (2) for feeding the raw material composition A, a heating tube (3), a heater (4), a gas-liquid separation tank (5), a circulation line (6) for the oligomer composition B, a circulation pump (7) for circulating the oligomer composition B, and an extraction line (8) for a vapor composition containing lactic acid.

The oligomer composition B is fed from the lower portion of the heating tube (3) by the circulation pump (7) for circulating the oligomer composition B, introduced into the gas-liquid separation tank (5) from the upper portion of the heating tube (3), and circulated through the circulation line (6) for the oligomer composition B. The raw material composition A is fed thereto from the feed pump (2) for feeding the raw material composition A and mixed therewith, and the resulting liquid mixture is fed to the heating tube (3). The heating tube (3) is heated with the heater (4) through the wall of the tube, and part of the liquid mixture is vaporized in the heating tube (3), extracted in the form of a gas-liquid mixture from the upper portion of the heating tube (3), and introduced into the gas-liquid separation tank (5). In the gas-liquid separation tank (5), the gas (vapor composition containing lactic acid) is separated from the liquid and extracted from the vaporizer through the extraction line (8) for a vapor composition containing lactic acid. The liquid is fed to the heating tube (3) again through the circulation line (6) for the oligomer composition B. In FIG. 1, the liquid mixture prepared by mixing the raw material composition A and the oligomer composition B is fed to the heating tube (3). Alternatively, the raw material composition A and the oligomer composition B may be separately fed to the heating tube (3) without mixing, and then mixed in the heating tube (3).

In this process, in order to balance the amounts (by weight) of the raw material composition A fed to the vaporizer and the vapor composition containing lactic acid extracted from the vaporizer, the feed rate of the raw material composition A, the feed rate of the oligomer composition B, the amount of heat applied to the heating tube, and the like are controlled. Thus, continuous and stable evaporation is achieved.

Figure 2:
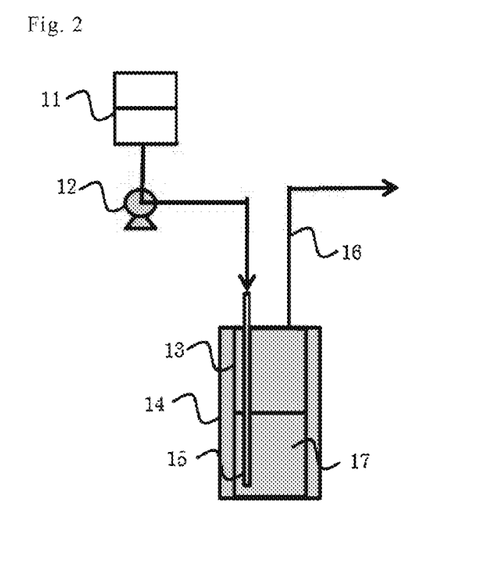
FIG. 2 illustrates a typical vaporizer of the present invention.

Alternatively, a simpler vaporizer as shown in FIG. 2 may be used. First, a heating vessel (13) is charged with an oligomer composition B (17). To the composition is fed the raw material composition A through a feed line (15) for the raw material composition A, and these compositions are mixed. A gas generated (vapor composition containing lactic acid) can be extracted through an extraction line (16) for a vapor composition containing lactic acid.

The present invention enables stable evaporation, leading to continuous and stable production of the vapor composition containing lactic acid. The amount of a lactic acid species in the vapor composition containing lactic acid in terms of lactic acid monomer is preferably 85 mol % or more, more preferably 90 mol % or more, still more preferably 95 mol % or more relative to the amount of a lactic acid species in the raw material composition A fed to the vaporizer in terms of lactic acid monomer. Here, the amount in terms of lactic acid monomer refers to the number of moles of lactic acid monomers in a lactic acid oligomer or lactide. For example, 1 mol of lactic acid dimer corresponds to 2 mol of lactic acid monomer, 1 mol of lactic acid trimer corresponds to 3 mol of lactic acid monomer, and 1 mol of lactide corresponds to 2 mol of lactic acid monomer.

Since an oligomer having a small polymerization degree, such as lactic acid dimer, has a certain level of vapor pressure, a lactic acid oligomer may be possibly contained in the vapor composition containing lactic acid depending on the lactic acid oligomer distribution in the liquid phase. For example, the resulting vapor composition containing lactic acid may be used in a reaction in the next step as long as the lactic acid oligomer contained in the vapor composition does not cause any problem.

The constitution of the vapor composition containing lactic acid varies depending on the constitution of the liquid mixture in the vaporizer. Therefore, in order to control the constitution of the vapor composition to a desired one, the constitution of the liquid mixture may be varied by, for example, controlling the pressure in the vaporizer, the heating temperature, the residence time of the liquid mixture in the vaporizer, the constitution of the raw material composition A, or other conditions.

It is preferred to mix the raw material composition A and the oligomer composition B as rapidly as possible. After the raw material composition A is brought into contact with the oligomer composition B, these compositions may be mixed using equipment including a stirrer or may be passed through a static type mixing device such as a static mixer.

Since evaporation is performed by the application of heat using a vaporizer, the vaporizer is preferably equipped with equipment enabling heat exchange (heat exchanger) in the industrial scale. Examples of the heat exchanger include thin film-type heat exchangers such as rising liquid film type exchangers, falling liquid film type exchangers, and agitated liquid film exchangers; plate-type heat exchangers; multitubular heat exchangers; and double pipe heat exchangers.

Examples of the vaporizer equipped with the heat exchanger include horizontal-tube or vertical-tube natural circulation vaporizers and forced circulation vaporizers.

The heating temperature in the vaporizer depends on factors such as the operating pressure and the constitutions of the vapor and the liquid, and thus is not particularly limited. Still, too high a temperature may cause pyrolysis of lactic acid or an oligomer, and therefore the maximum temperature in the vaporizer is preferably 350° C. or lower, more preferably 300° C. or lower, still more preferably 250° C. or lower. There may be a constitution distribution and a temperature distribution in the vaporizer, and thus the temperature in the vaporizer is not always kept constant and varies depending on the constitution of the liquid or occurrence of boiling. For example, in an apparatus as shown in FIG. 1, the outlet of the heating tube (3), at which a gas-liquid mixture is on the boil and the proportion of the vapor is highest, presumably has the highest temperature. Herein, this highest temperature is defined as an evaporation temperature. Therefore, the evaporation temperature of the vapor composition containing lactic acid is preferably 350° C. or lower, more preferably 300° C. or lower, still more preferably 250° C. or lower. The evaporation temperature is particularly preferably 200° C. or lower in terms of suppressing the generation of by-products. The evaporation temperature is preferably 100° C. or higher, more preferably 130° C. or higher. The pressure in the vaporizer is not particularly limited and is determined during the optimization of the entire process. The pressure is preferably 0.1 kPa or higher, more preferably 0.5 kPa or higher, still more preferably 10 kPa or higher, still further more preferably 50 kPa or higher. The pressure is preferably 4 MPa or lower, more preferably 3.5 MPa or lower, still more preferably 1 MPa or lower, still further more preferably 500 kPa or lower. The average residence time of the liquid phase in the vaporizer (liquid mixture in the vaporizer) is preferably 300 minutes or less, more preferably 240 minutes or less, still more preferably 180 minutes or less because too long an average residence time leads to pyrolysis of lactic acid or an oligomer. The average residence time is preferably 1 minute or more. In order to obtain lactic acid with good yield, the average residence time is more preferably 3 minutes or more, still more preferably 5 minutes or more. If the average residence time is less than 1 minute, the amount of the liquid in the vaporizer is small, which may lead to unstable operation.

In particular, as for the thermal history in the vaporizer, when the average residence time of the liquid mixture in the vaporizer at a temperature in the range of 210° C. or higher is set to 300 minutes or less, the pyrolysis of a lactic acid species can be suppressed and the vapor containing lactic acid can be obtained with high yield from the lactic acid species fed. The average residence time of the liquid mixture in the vaporizer at a temperature in the range of 210° C. or higher is more preferably 100 minutes or less, still more preferably 50 minutes or less, still further more preferably 30 minutes or less. In order to particularly suppress the generation of by-products, the average residence time is still further more preferably 10 minutes or less, particularly preferably 3 minutes or less.

The average residence time of the liquid mixture in the vaporizer herein is defined as a value obtained by dividing the volume of the liquid contained in the vaporizer at 40° C. or higher by the feed rate of the raw material composition A. The average residence time of the liquid mixture in the vaporizer at a temperature in the range of 210° C. or higher is defined as a value obtained by dividing the volume of the liquid contained in the vaporizer at 210° C. or higher by the feed rate of the raw material composition A.

The volume of the liquid mixture contained in the vaporizer at 40° C. or higher or 210° C. or higher can be calculated by obtaining the temperature distribution in the vaporizer using a thermometer and determining the volume of a portion at the corresponding temperature range in the vaporizer.

In cases where the raw material composition A with a high lactic acid concentration is used to increase the lactic acid concentration in the vapor composition containing lactic acid to a certain level, the water content of the oligomer composition B may be significantly smaller than the water content of the raw material composition A. In such a case, the residence time of the lactic acid species may be used as an indicator, which is defined as a value obtained by dividing the volume of the lactic acid species in the liquid mixture in the vaporizer by the feed rate of the lactic acid species in the raw material composition A. Similarly, the average residence time of the lactic acid species at a temperature in the range of 210° C. or higher is defined as a value obtained by dividing the volume of the lactic acid species in the liquid mixture in the vaporizer at a temperature of 210° C. or higher by the feed rate of the lactic acid species in the raw material composition A. As for the thermal history in the vaporizer with this indicator, when the average residence time of the lactic acid species at a temperature in the range of 210° C. or higher is set to 900 minutes or less, the pyrolysis of the lactic acid species can be suppressed and the vapor containing lactic acid can be obtained with high yield from the lactic acid species fed. The average residence time of the lactic acid species at a temperature in the range of 210° C. or higher is preferably 300 minutes or less, more preferably 150 minutes or less, still more preferably 50 minutes or less, particularly preferably 30 minutes or less.

Further, in the present invention, part of the liquid mixture is vaporized. If, for example, the whole liquid mixture is vaporized when heated, the temperature (boiling point) of the liquid increases as the vaporization proceeds, which may lead to the generation of loss of a lactic acid species due to pyrolysis, clogging caused by the attachment of heavy components such as an oligomer in the vaporizer, or a reduction in heat-transfer coefficient of the heating part. Further, if the liquid is dried, carbonaceous substances may be attached in the vaporizer. When only part of the liquid mixture is vaporized, the temperature change of the liquid mixture is small, and a vaporization portion of the liquid mixture always contains liquid, leading to less attachment of heavy components or carbonaceous substances to the wall of the tube of the vaporizer. Therefore, stable operation can be performed. For example, the percentage of the liquid mixture to be vaporized (hereinafter, also referred to as evaporation rate) in a vaporization portion such as, for example, the heating tube (3) is preferably 40% by mass or less, more preferably 30% by mass or less, still more preferably 20% by mass or less, still further more preferably 10% by mass or less of the liquid mixture introduced into the heating tube (3). If the percentage is more than 40% by mass, the volume of the vapor is too large relative to the volume of the liquid, which possibly causes a failure in stable operation.

Figure 1:
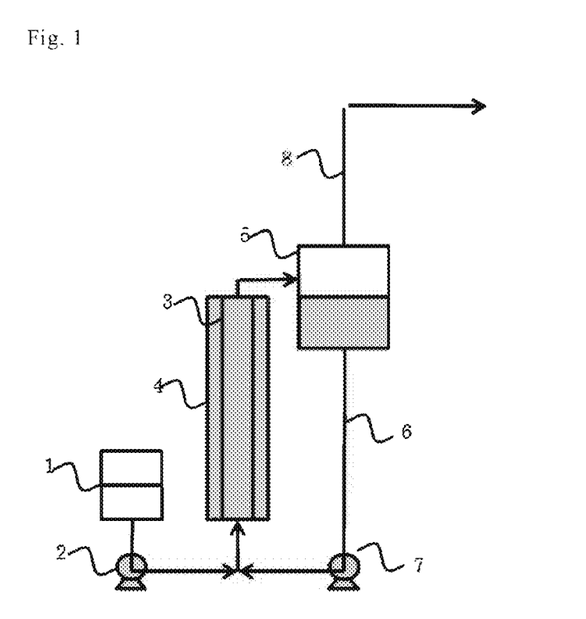
FIG. 1 illustrates a typical vaporizer of the present invention.

When an apparatus as shown in FIG. 1 is used, the raw material composition A is added to the circulating oligomer composition B. The amount of the oligomer composition B circulated is preferably 2 mass times or more, more preferably 3 mass times or more, still more preferably 5 mass times or more of the amount of the raw material composition A to be fed. The amount of the oligomer composition B circulated is preferably 1000 mass times or less, more preferably 500 mass times or less, still more preferably 200 mass times or less of the amount of the raw material composition A to be fed. If the amount of the oligomer composition B is less than 2 mass times of the amount of the raw material composition A, for example, the constitution in the heating tube may be significantly changed, causing unstable operation, or the evaporation rate in the heating tube may be increased, possibly leading to a reduction in heat-transfer coefficient. If the amount of the oligomer composition B is more than 1000 mass times of the raw material composition A, for example, a large-sized apparatus may be needed, or the pressure loss in the tube may be increased.

The raw material composition A may be fed to the vaporizer at room temperature or after pre-heating. When the raw material composition A is pre-heated, bumping of the raw material composition A can be suppressed, the temperature distribution in the vaporizer becomes small and the operation is stabilized, the heating load in the vaporizer is reduced, and other advantages are obtained. The temperature difference between the raw material composition A to be fed and a portion of the liquid of the oligomer composition B to which the raw material composition A is added is preferably 150° C. or lower, more preferably 100° C. or lower, still more preferably 50° C. or lower.

In addition to a liquid containing lactic acid, a lactic acid oligomer, and water, water or water vapor may be additionally fed as the raw material composition A, for example. Alternately, water in the raw material composition A may be reduced and then water or water vapor may be additionally fed to make up the reduced water. When water in the raw material composition A is reduced, the amount of lactic acid may be reduced and the amount of a lactic acid oligomer may be increased in the raw material composition A. Even in such a case, as long as the ratio between the total amount of water or water vapor fed and the amount of the lactic acid species is not changed and the liquid mixture is retained in the vaporizer for a time sufficient to achieve equilibrium between the oligomerization reaction and the hydrolysis reaction, the equilibrium constitution of the liquid mixture can be maintained constant. As a result, the vapor composition containing lactic acid is expected to be produced while its constitution is kept constant. In particular, when water vapor is additionally fed, the size of the heat exchanger can be more reduced and industrial evaporation can be more efficiently performed in cases where water vapor is produced using a boiler or the like than in cases where the aqueous solution of lactic acid is heated using the heat exchanger or the like of the vaporizer.

The lactic acid species may be evaporated while inert gas is introduced into the vaporizer. Examples of the inert gas include non-condensable gas such as nitrogen, helium, argon, carbon dioxide, or air. Multiple types of inert gas may be used in combination. The inert gas herein means gas inert to the lactic acid species in the form of liquid or gas in the evaporation of the lactic acid species. The amount of the inert gas fed may be from 0.01 times of the amount of the lactic acid to be fed to the equimolar amount of the lactic acid in terms of monomer, or may be more than the equimolar amount of the lactic acid.

In the production method of the present invention, long time operation may cause accumulation of heavy components in the liquid mixture in the vaporizer. In this case, the concentration of the heavy components in the system is kept constant by extracting part of the liquid mixture from the vaporizer. The method of extracting the part of the liquid mixture is, for example, extraction of part of the oligomer composition B through a circulation line of the vaporizer. The liquid mixture extracted may be disposed, or lactic acid in the liquid mixture may be collected and reused, or a lactic acid oligomer or lactide in the liquid mixture may be decomposed by hydrolysis into lactic acid and the lactic acid may be collected and reused.

The lactic acid species has very high corrosivity, and exhibits significant corrosivity particularly at high temperatures exceeding 200° C. Therefore, the material of the vaporizer preferably has a certain level of corrosion resistance to the lactic acid species. Examples of the material having corrosion resistance to the lactic acid species include austenitic stainless steel, ferrite stainless steel, duplex stainless steel, nickel alloy, titanium, zirconium, tantalum, titanium alloy, gold, and platinum. The vapor composition containing lactic acid obtained as described above can be converted into other useful chemicals by bringing the composition into contact with a catalyst. Examples of products formed from the lactic acid species include acrylic acid and pyruvic acid.

The production method of the present invention is useful particularly for the synthesis of acrylic acid. Acrylic acid can be produced by bringing the vapor composition containing lactic acid obtained according to the present invention into contact with a dehydration catalyst. The resulting reaction gas is cooled or brought into contact with a collection liquid to be collected and liquefied, and then purified by extraction, distillation, crystallization, or the like. Thus, acrylic acid with high purity can be obtained. Acrylic acid is widely used as a raw material of water-absorbing resins, coating materials, or adhesives.

EXAMPLE

The present invention is specifically described with reference to examples and comparative examples, but is not limited to these examples below.

(Analysis Conditions for Liquid Chromatography)
Body: L-2000 series (Hitachi High-Technologies Corporation.)
Column: Inertsil ODS-4 (GL Sciences Inc.)×1
Eluent: Acetonitrile/Water/Phosphoric acid/Potassium dihydrogenphosphate=40/58.5/1.0/0.5 (weight ratio)
Detector: UV 205 nm
Column temperature: 50° C.
Eluent flow rate: 0.5 ml/min
(Analysis Conditions 1 for Gas Chromatography)
Body: GC-2014 (Shimadzu Corporation)
Column: ULBON HR-20M (Shinwa Chemical Industries, Ltd., inner diameter: 0.53 mm, length: 30 m, thickness: 5 μm)
Detector: FID
Vaporizer temperature: 270° C.
Detector temperature: 270° C.
Carrier gas: Helium
Carrier gas flow rate: 10 ml/min
(Analysis Conditions 2 for Gas Chromatography)
Body: GC-2014 (Shimadzu Corporation)
Column: Shincarbon ST 50/80 (Shinwa Chemical Industries, Ltd.), inner diameter: 3 mm, length: 2 m
Detector: TCD
Vaporizer temperature: 260° C.
Detector temperature: 260° C.
Carrier gas: Helium
Carrier gas flow rate: 40 ml/min Example 1

A stainless-steel vaporizer (inner diameter: 23.4 mm, height: 120 mm) equipped with a feed line (15) for the raw material composition A, an extraction line (16) for a vapor composition containing lactic acid, and a thermometer, as shown in FIG. 2, was charged with 12 g of a 90% by mass aqueous solution of lactic acid. The solution was heated to a predetermined temperature with an oil bath. Thereafter, a 20% by mass aqueous solution of lactic acid was fed to the liquid phase in the vaporizer at a flow rate of 0.2 ml/min, and mixed with the liquid in the vaporizer. Separately, nitrogen was passed through the gas phase in the vaporizer at a flow rate of 52 ml/min.

The vaporized gas was extracted through the extraction line (16) and cooled with a cooler. Thereby, a condensate was collected in a receiver. The temperature of the oil bath was controlled such that the distillation rate of the condensate was equal to the feed rate of the raw material. The distillation rate was equal to the feed rate when the temperatures of the oil bath and the liquid in the vaporizer were 210° C. and 200° C., respectively. Then, the evaporation was continued for nine hours while these temperatures were kept.

The receiver containing the resulting condensate was replaced every one hour, and each condensate was analyzed by liquid chromatography. The results of the analysis showed that the condensates obtained after the lapse of one hour had the same, stable constitution. The condensates each consisted of 13.1% by mass of lactic acid, 5.7% by mass of lactic acid dimer, and 0.3% by mass of lactic acid trimer, with the balance being water. No by-products were detected. The analysis also confirmed that the amount of lactic acid fed in the raw material was 26.7 mmol/h and the amount of a lactic acid species in the condensate was 26.7 mmol/h in terms of lactic acid monomer, i.e., the feed rate and distillation rate of the lactic acid monomer were the same as each other. The condensate was analyzed by gas chromatography (analysis conditions 1), and the gas components after condensation were analyzed by gas chromatography (analysis conditions 2). Products other than a lactic acid species were not detected.

The liquid phase (oligomer composition B) at the termination of the evaporation was analyzed for its constitution. The water content, which was measured using a Karl Fischer analyzer, was 0.5% by mass. In addition, the constitution of the lactic acid species was analyzed by liquid chromatography and the constitution shown in the following table was obtained.

TABLE 1

|  | Monomer | Dimer | Trimer | Tetramer | Pentamer | Hexamer | Heptamer | Octamer | Nonamer | Decamer |
|---|---|---|---|---|---|---|---|---|---|---|
| % by mass | 14.4 | 12.5 | 13.1 | 12.5 | 10.8 | 9.0 | 7.5 | 5.0 | 4.1 | 3.1 |

The total amount of the lactic acid monomer to the lactic acid decamer was 92.0% by mass. Lactic acid oligomers having a high molecular weight containing 11 or more lactic acid monomer units were detected, but not quantified. The weight ratio of the lactic acid dimer to the lactic acid monomer in the oligomer composition B (lactic acid dimer/lactic acid monomer) was 0.87.

This example showed that the 20% by mass aqueous solution of lactic acid (raw material composition A) was mixed with the solution (oligomer composition B) contained in the vaporizer having the constitution shown in the above table and then the vapor components were obtained from the liquid mixture, and showed that the amount of the lactic acid species in the vapor components was approximately the same as the amount of the lactic acid fed in terms of lactic acid monomer.

Comparative Example 1

A quartz tube with an outer diameter of 9 mm, an inner diameter of 7 mm, and a length of 35 cm was inserted into a stainless steel tube with an inner diameter of 10 mm. The quartz tube was filled with 7.85 ml of quartz beads with a diameter of 710 μm to 2 mm to prepare a vaporizer. The vaporizer was heated from the outside with an electric heater. A 20% by mass aqueous solution of lactic acid and nitrogen were fed to the upper portion of the vaporizer at flow rates of 0.05 ml/min and 55 ml/min, respectively. The output of the electric heater was controlled so that the aqueous solution of lactic acid fed was substantially completely extracted. In the vaporizer, the temperature around the inlet was 105° C. and the temperature around the outlet was 301° C. The vapor extracted from the outlet of the vaporizer was cooled with a cooler. Thereby, a condensate was collected in a receiver. The condensate was analyzed by liquid chromatography, and found to contain 15.4% by mass of lactic acid and 3.7% by mass of lactic acid dimer.

In addition, the condensate and the gas components obtained after condensation were analyzed by gas chromatography (under analysis conditions 1) and by gas chromatography (under analysis conditions 2), respectively, and were found to contain 1.1 mol % of acetaldehyde, 0.3 mol % of hydroxy acetone, 0.2 mol % of acetic acid, 1.2 mol % of propionic acid, 0.6 mol % of acrylic acid, 1.0 mol % of carbon monoxide, and 0.2 mol % of carbon dioxide as by-products relative to the amount of the lactic acid fed.

The production rate of each by-product was calculated using the following formula:

((the number of moles of each by-product×the number of carbon atoms)/(the number of moles of lactic acid fed×3))×100.

After the experiment, the quartz beads were stained with brownish, and carbonaceous powder was attached to the beads.

In this comparative example, the 20% by mass aqueous solution of lactic acid was directly fed to the vaporizer without mixing with the liquid containing a lactic acid oligomer and evaporation of the whole liquid was targeted, but many by-products were generated. In addition, a lactic acid oligomer composed of three or more lactic acid monomer units was left in the vaporizer, leading to the generation of loss of a lactic acid species.

Example 2

(Preparation of Vaporizer)

The apparatus shown in FIG. 1 was prepared using the following instruments:

Tank (1) for the raw material composition A: 5 L-Tank made of polyethylene

Feed pump (2) for feeding the raw material composition A: Seram Q pump (Yamazen Corporation)

Heating tube (3): Tube made of JIS type 2 titanium (inner diameter: 10.0 mm, height: 600 mm)

Heater (4): Micro heater (voltage: 100 V, electrical capacitance: 600 W, length: 4000 mm) wound spirally around the heating tube (3)

Gas-liquid separation tank (5): Tube made of JIS type 2 titanium (inner diameter: 21.2 mm, length: 800 mm)

Circulation line (6) for the oligomer composition B: Tube made of JIS type 2 titanium (inner diameter: 4.0 mm, length: 1000 mm)

Circulation pump (7) for circulating the oligomer composition B: Seram Q pump (Yamazen Corporation)

Extraction line (8) for a vapor composition containing lactic acid: Tube made of JIS type 2 titanium connected to a cooler for condensation of a vapor composition In addition to these instruments, the tubes were connected using a stainless steel joint available from Swagelok, and all the heating parts were protected with a thermal tube made of glass wool. An insert tube made of JIS type 2 titanium was inserted into the heating tube and the gas-liquid separation tank to appropriately measure the temperatures. Furthermore, in order to control the pressure in the apparatus, an electronically controlled back pressure regulator ER5000 (Tescom) and a mass flow controller SLA5850S (ITW Japan) were used, and a high purity nitrogen cylinder (Sumitomo Seika Chemicals Company Limited) was used as a source of an inert gas. In addition, a differential pressure sensor DP-15 (Validyne) was used to keep the liquid level unchanged in the gas-liquid separation tank.

The volume of the liquid in the vaporizer composed of the above instruments, that is, the volume except for empty portions, was 326 mL.

Example 2-1

(Preparation of Solution of Lactic Acid Oligomer)

The liquid mixture circulation vaporizer prepared as described above was charged with 326 ml of a 90% by mass aqueous solution of lactic acid (special grade reagent, Wako Pure Chemical Industries, Ltd.), and the pressure in the system was set to 0.1 MPa using an electronically back pressure regulator while nitrogen was introduced at a flow rate of 10 ml/min. Furthermore, the circulation pump (7) for circulating the oligomer composition B was operated at a flow rate of 20 ml/min and the reagent was heated with the heater (4) while being circulated so that water was distilled off. Thus, oligomerization was enhanced. The evaporated water was extracted through the extraction line (8) and cooled with the cooler. Thereby, a condensate was collected in a receiver. A 90% by mass aqueous solution of lactic acid was fed from the feed pump (2) for feeding the raw material composition A in accordance with the amount of water distilled off so that the amount of the liquid in the vaporizer was kept unchanged. The feeding of the 90% by mass aqueous solution of lactic acid was stopped when the temperature of the liquid in the upper portion of the heating tube (3) reached 160° C.

(Production of Vapor Composition Containing Lactic Acid)

After the solution of a lactic acid oligomer was prepared, a raw material aqueous solution containing 20.3% by mass of lactic acid and 0.4% by mass of lactic acid dimer was fed at a flow rate of 2 ml/min under the conditions of a pressure in the vaporizer of 0.1 MPa, a flow rate of the circulation pump (7) for circulating the oligomer composition B of 20 ml/min, and a nitrogen flow rate of 10 ml/min. At this time, the residence time of the liquid in the vaporizer was calculated to be 163 minutes. The temperature of the heating tube was controlled so that the distillation rate of the condensate was equal to the feed rate of the raw material. The distillation rate was equal to the feed rate of the raw material when the temperatures of the heater (4) and the liquid at the upper portion of the heating tube (3) reached 168° C. and 163° C., respectively. The evaporation was continued for four hours while these temperatures were kept. The receiver containing the obtained condensate was replaced every half hour, and each condensate was analyzed by liquid chromatography and gas chromatography (analysis conditions 1). The results of the analysis showed that the condensates obtained after the lapse of half hour had the same, stable constitution. The condensates each consisted of 16.9% by mass of lactic acid, 2.4% by mass of lactic acid dimer, and 0.2% by mass of lactic acid trimer, with the balance being water. No by-products were detected. The analysis also confirmed that the amount of a lactic acid species in the raw material was 288 mmol/h in terms of lactic acid monomer and the amount of a lactic acid species in the condensate was 280 mmol/h in terms of lactic acid monomer, and as a result, the percentage of the distillate in terms of lactic acid monomer (also referred to as distillation percentage of a lactic acid species) was calculated to be 97%. Thus, according to this example, the vapor composition containing lactic acid can be produced stably for a long time with a high distillation percentage of a lactic acid species. The gas components after condensation were analyzed by gas chromatography (analysis conditions 2). Products other than a lactic acid species were not detected.

The temperature of the raw material aqueous solution was 50° C., and the temperature of a portion of the solution of a lactic acid oligomer to which the raw material aqueous solution was added was 150° C. The difference between these temperatures was 100° C.

The liquid phase (oligomer composition B) at the termination of the evaporation was analyzed for its constitution.

The amount of the lactic acid species was analyzed by liquid chromatography and the water content was analyzed using a Karl Fischer analyzer, and the constitutions shown in Table 4 were obtained.

At this time, the mass ratio of the lactic acid dimer to lactic acid in the oligomer composition B was 0.87.

Tables 2 to 4 below show the results of Example 2-1. In Table 3 below, the term "constitution of distillate" means the proportions (mol %) of lactic acid, a lactic acid oligomer, and by-products, excluding water.

Examples 2-2 to 2-7

Experiments were performed as in the above examples, except that the pressure, the concentration of the raw material, the amount of the raw material fed, and the flow rate of the circulation pump were changed. The conditions and the results of the examples are shown in the tables below.

In Tables 2 to 4, AD expresses acetaldehyde, PA expresses propionic acid, AA expresses acrylic acid, and CO expresses carbon monoxide.

TABLE 2

| Example | Pressure (MPa) | Average residence time (min) | Evaporation temperature (°C.) | Concentration of raw material (% by mass) | | | Flow rate of raw material (ml/min) | Circulation flow rate (ml/min) | Amount of lactic acid in flow of raw material *1 (mmol/h) | Residence time at 210°C. or higher (min) |
|---|---|---|---|---|---|---|---|---|---|---|
| | | | | Lactic acid | Lactic acid dimer | Lactic acid trimer | | | | |
| 2-1 | 0.1 | 163 | 163 | 20.3 | 0.4 | 0.0 | 2 | 20 | 288 | 0 |
| 2-2 | 0.1 | 58 | 163 | 20.3 | 0.4 | 0.0 | 4 | 241 | 605 | 0 |
| 2-3 | 0.1 | 163 | 165 | 20.3 | 0.4 | 0.0 | 2 | 241 | 301 | 0 |
| 2-4 | 0.3 | 115 | 193 | 20.3 | 0.4 | 0.0 | 2 | 241 | 309 | 0 |
| 2-5 | 0.3 | 163 | 193 | 20.3 | 0.4 | 0.0 | 2 | 20 | 288 | 0 |
| 2-6 | 0.6 | 41 | 214 | 20.3 | 0.4 | 0.0 | 8 | 80 | 1142 | 6 |
| 2-7 | 0.49 | 20 | 243 | 33.4 | 1.4 | 0.0 | 16 | 160 | 4003 | 6 |

*1 In terms of lactic acid monomer

TABLE 3

| Example | Distillation percentage of lactic acid and derivatives thereof (%) | Constitution of distillate (mol %) | | | | | | | Amount of lactic acid in distillate *2 (mmol/h) |
|---|---|---|---|---|---|---|---|---|---|
| | | Lactic acid | Lactic acid dimer | Lactic acid trimer | AD | PA | AA | CO | |
| 2-1 | 97 | 85.3 | 13.4 | 0.9 | 0.0 | 0.0 | 0.0 | 0.0 | 280 |
| 2-2 | 100 | 76.5 | 20.1 | 3.3 | 0.0 | 0.0 | 0.0 | 0.0 | 605 |
| 2-3 | 98 | 85.7 | 12.6 | 1.8 | 0.0 | 0.0 | 0.0 | 0.0 | 296 |
| 2-4 | 99 | 78.8 | 16.0 | 4.5 | 0.3 | 0.0 | 0.1 | 0.2 | 307 |
| 2-5 | 97 | 87.3 | 10.8 | 1.3 | 0.3 | 0.0 | 0.1 | 0.1 | 279 |
| 2-6 | 100 | 83.9 | 13.7 | 0.8 | 1.0 | 0.1 | 0.1 | 0.5 | 1123 |
| 2-7 | 97 | 80.4 | 15.3 | 1.7 | 0.5 | 0.1 | 0.1 | 0.2 | 3896 |

*2 In terms of lactic acid monomer

TABLE 4

| Example | Constitution of liquid phase (% by mass) | | | | | | | | | | | Lactic acid dimer/ Lactic acid (mass ratio) |
|---|---|---|---|---|---|---|---|---|---|---|---|---|
| | Lactic acid | Lactic acid dimer | Lactic acid trimer | Lactic acid tetramer | Lactic acid pentamer | Lactic acid hexamer | Lactic acid heptamer | Lactic acid octamer | Lactic acid nonamer | Lactic acid decamer | Water | |
| 2-1 | 24.7 | 21.6 | 18.7 | 12.4 | 7.7 | 4.6 | 2.7 | 1.7 | 0.8 | 0.0 | 1.6 | 0.87 |
| 2-2 | 23.8 | 23.8 | 18.2 | 13.1 | 8.6 | 5.6 | 2.5 | 1.5 | 0.9 | 0.0 | 1.7 | 1.00 |
| 2-3 | 21.0 | 22.8 | 18.6 | 13.9 | 9.9 | 7.0 | 4.7 | 2.7 | 1.6 | 0.0 | 1.6 | 1.08 |
| 2-4 | 35.9 | 25.3 | 15.8 | 9.1 | 4.9 | 2.6 | 1.3 | 0.7 | 0.1 | 0.0 | 3.3 | 0.70 |
| 2-5 | 28.7 | 23.3 | 16.1 | 10.5 | 6.6 | 3.8 | 2.2 | 1.3 | 0.2 | 0.0 | 2.9 | 0.81 |
| 2-6 | 41.7 | 26.6 | 14.4 | 6.8 | 3.1 | 1.6 | 0.7 | 0.0 | 0.0 | 0.0 | 5.0 | 0.64 |
| 2-7 | 16.9 | 18.7 | 16.5 | 13.9 | 11.0 | 7.4 | 5.8 | 4.3 | 2.8 | 1.9 | 1.3 | 1.10 |

These examples demonstrate that as the residence time at 210° C. or higher decreases, the collection rate of a lactic acid species increases and the generation of by-products is more prevented.

INDUSTRIAL APPLICABILITY

The method for producing a vapor composition containing lactic acid of the present invention is capable of preventing the generation of by-products such as acetaldehyde and carbon monoxide due to pyrolysis of a lactic acid species during vaporization. Furthermore, a lactic acid oligomer generated during vaporization can be effectively used without loss, and the evaporation efficiency of lactic acid can be enhanced. In addition, the attachment of heavy compounds such as an oligomer can be prevented. Therefore, the method of the present invention can be used to industrially efficiently produce a vapor composition containing lactic acid stably for a long time.

REFERENCE SIGNS LIST

1: Tank for raw material composition A
2: Feed pump for feeding raw material composition A
3: Heating tube
4: Heater
5: Gas-liquid separation tank
6: Circulation line for oligomer composition B
7: Circulation pump for circulating oligomer composition B
8: Extraction line for vapor composition containing lactic acid
11: Tank for raw material composition A
12: Feed pump for feeding raw material composition A
13: Heating vessel
14: Heater
15: Feed line for raw material composition A
16: Extraction line for vapor composition containing lactic acid
17: Oligomer composition B

The invention claimed is:

1. A method for producing a vapor composition containing lactic acid comprising:
   mixing a liquid composition containing lactic acid fed to a vaporizer with a liquid composition containing a lactic acid oligomer contained in the vaporizer to prepare a liquid mixture; and
   heating the liquid mixture to vaporize part of the liquid mixture, whereby a vapor composition containing lactic acid is produced.

2. The method for producing a vapor composition containing lactic acid according to claim 1,
   wherein a mass ratio of lactic acid dimer to lactic acid (lactic acid dimer/lactic acid) contained in the liquid composition containing a lactic acid oligomer is 0.4 to 3.

3. The method for producing a vapor composition containing lactic acid according to claim 1,
   wherein an average residence time of the liquid mixture in the vaporizer at a temperature in the range of 210° C. or higher is 300 minutes or less.

4. The method for producing a vapor composition containing lactic acid according to claim 1,
   wherein an average residence time of the liquid mixture in the vaporizer is 1 minute or more and 300 minutes or less.

5. The method for producing a vapor composition containing lactic acid according to claim 1,
   wherein the vaporizer has an internal pressure of 0.1 kPa or higher and 4 MPa or lower.

6. The method for producing a vapor composition containing lactic acid according to claim 1,
   wherein an evaporation temperature of the vapor composition containing lactic acid is 100° C. or higher and 350° C. or lower.

7. The method for producing a vapor composition containing lactic acid according to claim 1,
   wherein the liquid composition containing a lactic acid oligomer contained in a vaporizer includes lactic acid oligomers from dimer to decamer in a total amount of 50% by mass or more based on the entire lactic acid oligomer.

8. The method for producing a vapor composition containing lactic acid according to claim 1,
   wherein a temperature difference between the liquid composition containing lactic acid fed to a vaporizer and a portion of the liquid composition containing a lactic acid oligomer contained in the vaporizer to which the liquid composition containing lactic acid is added is 150° C. or lower.

9. The method for producing a vapor composition containing lactic acid according to claim 1,
   wherein an amount of a lactic acid species in the vapor composition containing lactic acid in terms of lactic acid monomer is 85 mol % or more relative to an amount of a lactic acid species in the liquid composition containing lactic acid fed to a vaporizer in terms of lactic acid monomer.

* * * * *